(12) United States Patent
Arunakumari et al.

(10) Patent No.: US 8,129,508 B2
(45) Date of Patent: Mar. 6, 2012

(54) PROTEIN PURIFICATION USING HCIC AND ION EXCHANGE CHROMATOGRAPHY

(75) Inventors: Alahari Arunakumari, Pennington, NJ (US); Gisela Maria Marques Ferreira, Fountain Hill, PA (US)

(73) Assignee: Medarex, Inc., Princeton, NJ (US)

( * ) Notice: Subject to any disclaimer, the term of this patent is extended or adjusted under 35 U.S.C. 154(b) by 121 days.

(21) Appl. No.: 11/918,155

(22) PCT Filed: Mar. 21, 2006

(86) PCT No.: PCT/US2006/010412
§ 371 (c)(1),
(2), (4) Date: Dec. 16, 2008

(87) PCT Pub. No.: WO2006/110277
PCT Pub. Date: Oct. 19, 2006

(65) Prior Publication Data
US 2009/0105465 A1    Apr. 23, 2009

Related U.S. Application Data

(60) Provisional application No. 60/670,457, filed on Apr. 11, 2005.

(51) Int. Cl.
*C07K 16/00* (2006.01)
*C07K 1/18* (2006.01)
*C07K 1/20* (2006.01)

(52) U.S. Cl. ............... 530/415; 530/391.1; 530/390.5; 530/416

(58) Field of Classification Search .............. None
See application file for complete search history.

(56) References Cited

U.S. PATENT DOCUMENTS

| 7,138,262 B1 * | 11/2006 | Daniel | 435/201 |
|---|---|---|---|
| 7,323,553 B2 * | 1/2008 | Fahrner et al. | 530/412 |
| 2003/0229212 A1 * | 12/2003 | Fahrner et al. | 530/417 |
| 2004/0033535 A1 | 2/2004 | Boyle et al. | |
| 2010/0190210 A1 * | 7/2010 | Arunakumari et al. | 435/69.6 |

FOREIGN PATENT DOCUMENTS

| WO | WO-02/15927 A1 | 2/2002 |
| WO | WO-2005/049649 A1 | 6/2005 |
| WO | WO 2007/108955 | 9/2007 |

OTHER PUBLICATIONS

Boschetti, Egisto, "Antibody separation by hydrophobic charge induction chromatography," *Trends in Biotechnology*, vol. 20(8):333-337 (2002).

Follman, Deborah K. et al., "Factorial screening of antibody purification processes using three chromatography steps without protein A," *Journal of Chromatography A*, vol. 1024:79-85 (2004).

Guerrier, L. et al., "New method for the selective capture of antibodies under physiological conditions," *Bioseparation*, vol. 9:211-221 (2000).

Schwartz, Warren et al., "Comparison of hydrophobic charge induction chromatography with affinity chromatography on protein A for harvest and purification of antibodies," *Journal of Chromatography A*, vol. 908:251-263 (2001).

International Preliminary Report on Patentability for Application No. PCT/US2006/010412, dated Oct. 16, 2007.

* cited by examiner

*Primary Examiner* — David A Saunders
(74) *Attorney, Agent, or Firm* — Z. Angela Guo (57) ABSTRACT

The present invention provides methods for purifying proteins. In particular, the methods employ a two-step non-affinity chromatography process without the use of an in-process tangential flow filtration step.

38 Claims, 1 Drawing Sheet

Purified (therapeutic) Protein Material

PROTEIN PURIFICATION USING HCIC AND ION EXCHANGE CHROMATOGRAPHY

FIELD OF THE INVENTION

This invention relates generally to protein purification using a two-step non-affinity chromatography process without the use of an in-process tangential flow filtration step. In particular, the invention relates to a method for purifying polypeptides (such as recombinant proteins, antibodies, antibody fragments, Fab and Fv related products, single-chain antibodies, diabodies, linear antibodies, bispecific antibodies, multispecific antibodies including those from antibody fragments, fusion proteins with Fc like regions and antibody-like molecules, e.g. immunoadhesins) from a composition comprising the polypeptide and one or more contaminants.

BACKGROUND OF THE INVENTION

The large-scale, economic purification of proteins is an increasingly important problem for the biopharmaceutical industry. Therapeutic proteins are typically produced using prokaryotic or eukaryotic cell lines that are engineered to express the protein of interest from a recombinant plasmid containing the gene encoding the protein. Separation of the desired protein from the mixture of components fed to the cells and cellular by-products to an adequate purity, e.g., sufficient for use as a human therapeutic, poses a formidable challenge to biologics manufacturers for several reasons.

Manufacturers of protein-based pharmaceutical products must comply with strict regulatory standards, including extremely stringent purity requirements. To ensure safety, regulatory agencies, such as Food and Drug Administration (FDA), require that protein-based pharmaceutical products are substantially free from impurities, including both product related contaminants such as aggregates, fragments and variants of the recombinant protein and process related contaminants such as host cell proteins, media components, viruses, DNA and endotoxins. While various protein purification schemes are available and widely used in the biopharmaceutical industry, they typically include an affinity-purification step, such as Protein A purification in the case of antibodies, in order to reach a pharmaceutically acceptable degree of purity.

Despite the advent of advanced chromatography and filtration methods, affinity chromatography is still often employed as a capture step to meet the purity, yield, and throughput requirements for biopharmaceutical antibody purification in order to achieve therapeutic grade purity. Despite a high binding affinity of Protein A chromatography for antibodies (about $10^{-8}$ M for human IgG), and ability to remove as much as 99.5% of impurities, affinity chromatography is an expensive purification step for use in purifying therapeutic proteins on a commercial scale. Not only is Protein A significantly more expensive than non-affinity media, it also has problems such as resin instability, difficulty with cleaning, ligand leakage, and potential immunogenicity of Protein A or Protein A related compounds contaminating the purified product. The high cost and instability of affinity media, however, increases the ultimate cost of protein-based therapeutics, particularly those requiring high doses and/or chronic administration. Chromatography alone can account for two thirds of downstream processing costs and, with respect to monoclonal antibodies, the resin cost for an affinity-capture column can overwhelm raw materials cost. (see Rathore et al, Costing Issues in the Production of Biopharmaceuticals, BioPharm International, Feb. 1, 2004).

Even if Protein A affinity chromatography is used, adequate purity is often not achieved unless several purification steps are combined, thereby further increasing cost and reducing product yield. Since antibodies account for an increasingly large percentage of therapeutic biologics on the market and in development for the treatment of cancer, autoimmune disease, infectious disease, cardiovascular disease, and transplant rejection, there is a need for a process that can purify proteins using fewer steps and thus realizing lower cost.

US Pat. Pub. No. 2003/0229212, which is hereby incorporated by reference in its entirety, describes a method for purifying antibodies from a mixture containing host cell proteins using non-affinity chromatography purification steps followed by a high-performance tangential-flow filtration (HPTFF) step. As determined by the reduction of CHOPs (Chinese Hamster Ovary cell Proteins), that purification process resulted in contaminant levels of about 144,780 ppm CHOPs after cation exchange purification, about 410 ppm CHOPs after anion exchange purification, and about 17-21 ppm CHOPs after HPTFF purification (final step), thereby providing a three-step non-affinity process. The purification step of HPTFF, which uses a charged membrane to separate impurities (without limit to relative size), such as proteins, DNA and endotoxins, and to eliminate protein oligomers and degradation products from the mixture containing the antibodies, was essential to achieve the final purity.

Moreover, HPTFF has disadvantages, namely (1) it is an extra step in the development, optimization and scale-up of the protein therapeutic, which requires membrane cleaning, validation, commercial availability of large-scale GMP cassettes (which is not yet available for HPTFF), and additional buffers, equipment and greater process time, and (2) it increases costs while risking potential loss of product by compromising antibody integrity (by degradation or aggregation or other molecular change that affects molecular activity).

Therefore, it would be desirable to obtain high purity of a protein therapeutic from a two-step, non-affinity process, which is not based on HPTFF, at a reduced cost in comparison with affinity-based purification and other multi-step purification processes. It would be advantageous if the non-affinity purification process could remove host cell proteins, nucleic acids, endotoxins, product-related contaminants, e.g., aggregated, oxidized, deamidated or degraded forms of the protein, and media additives, e.g., lipids, vitamins, insulin, methotrexate, amino acids, carbon sources such as glucose, etc.

The development of a purification scheme applicable to various types of proteins, scaleable, controllable, and that employs cheaper, reusable resins will allow its integration into product development at a very early stage in overall drug development. This approach to the design of a purification scheme can minimize costly changes to manufacturing processes which may otherwise be necessary later in drug development or, worse, after approval. As the process is scaled-up and approaches GMP production conditions, additional inherent complexities arise, including those associated with resin packing and buffer preparation. The manufacturing process, and its capacity, can be improved by simplifying the purification scheme by eliminating process steps and maximizing throughput and productivity, while maintaining the integrity and purity of the molecule that is being purified. Therefore, it would be desirable and advantageous to start with a simple and efficient process that can produce a drug substance of high quality and safety.

SUMMARY OF THE INVENTION

The present invention is based on the unexpected finding that polypeptides and proteins, in particular recombinant proteins such as monoclonal antibodies, can be purified from a contaminated mixture comprising the molecule of interest and at least one contaminant, such as host cell proteins and other materials such as media components, by using a two-step purification process that does not include an affinity chromatography step or an in-process buffer exchange step (e.g., TFF or HPTFF). Rather, only pH manipulations are necessary from the first step to the second step. The two-step process of the present invention, therefore, substantially reduces the cost of purifying proteins that typically rely on affinity chromatography or multi-step methodologies to achieve similarly high levels of protein purity.

In the present invention, proteins are highly purified to a therapeutic grade using the steps of cation exchange chromatography and hydrophobic charge induction chromatography, without regard to their order and without the use of affinity chromatography, in order to yield a high-purity protein composition that contains negligible amounts of impurities [e.g., host cell proteins, such as CHOPs in amounts less than 100 parts per million (ppm)]. In particular embodiments of the invention, described in the Example infra., HCP CHOP levels were reduced to less than 20 ppm. It is an advantage of a method of the present invention that the chromatography steps are interchangeable, thereby allowing practitioners to tailor the method to their needs. Furthermore, a purification process of the present invention can remove not only host cell protein of interest, but also nucleic acids, endotoxins, product-related contaminants, such as aggregated, oxidized, deamidated or degraded forms of the protein, and media additives, e.g., lipids, vitamins, insulin, methotrexate, amino acids, carbon sources such as glucose, etc.

The present invention provides methods for the purification of recombinant proteins including, but not limited to antibodies, fusion proteins with Fc like regions, and antibody-like molecules, e.g. immunoadhesins, in order to achieve a highly pure protein composition suitable for use in preparing therapeutic grade compositions. As a result, it is an advantage of a method of the present invention that the highly pure protein composition is suitable for use in preparing therapeutic grade material and can be used directly in human therapy.

Thus, in one embodiment, a method of the invention is directed to purifying a mixture that contains a target protein and one or more contaminants by (a) subjecting the mixture to an ion exchange purification step and a hydrophobic charge induction purification step, where there is no in-process tangential flow filtration step, and (b) isolating the target protein.

In a particular embodiment, the method is directed to purifying a mixture that contains a target protein and one or more contaminants such as host cell proteins (e.g., CHOPs) and nucleic acids by subjecting the mixture to cation exchange chromatography and to hydrophobic charge induction chromatography, and isolating the target protein to a purity of 100 parts per million (ppm) or less of host cell protein and 10 pg/mg or less of nucleic acids.

DETAILED DESCRIPTION OF THE INVENTION

Definitions

As used herein, "protein" refers generally to peptides and proteins typically having at least 5 amino acids or more which are linked together by peptide bonds. A protein can be an antibody, receptor, ligand fusion protein (which comprise at least a portion of two or more polypeptides that are not fused in their natural state), etc., e.g., see US2003022921 and US 20030166869 which are hereby incorporated by reference in their entireties and which list various proteins that can be purified according to a method of the invention. Polypeptides can be from any organism (prokaryotic or eukaryotic), particularly from mammals. In addition, a protein or polypeptide purified according to a method of the invention can be an antibody, fragment, or a variant thereof.

The term "antibody" is used in the broadest sense to cover monoclonal antibodies (including full length monoclonal antibodies), polyclonal antibodies, multispecific antibodies (e.g., bispecific antibodies), immunoadhesins and antibody fragments so long as they retain, or are modified to comprise, a ligand-specific binding domain. An antibody can be directed against an "antigen" of interest, such as a polypeptide, which may be a biologically relevant therapeutic target, or a non-polypeptide antigen (e.g, such as tumor-associated glycolipid antigens; see U.S. Pat. No. 5,091,178). Preferably, the antigen is a biologically important polypeptide and administration of the antibody to a mammal suffering from a disease or disorder can result in a therapeutic benefit in that mammal. Polypeptide antigens include transmembrane molecules (e.g. receptor) and ligands such as growth factors. Exemplary antigens include those polypeptides discussed above. The preparation of antigens for generating antibodies and antibody production are well known in the art. Soluble antigens, or fragments thereof optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

An "antibody fragment" includes at least a portion of a full length antibody and typically an antigen binding or variable region thereof. Examples of antibody fragments include Fab, Fab', F(ab)$_2$, and Fv fragments; single-chain antibody molecules; diabodies; linear antibodies; and multispecific antibodies formed from antibody fragments.

The term "monoclonal antibody" is used in the conventional sense to refer to an antibody obtained from a population of substantially homogeneous antibodies such that the individual antibodies comprising the population are identical except for possible naturally occurring mutations that may be present in minor amounts. Monoclonal antibodies are highly specific, being directed against a single antigenic site. This is in contrast with polyclonal antibody preparations which typically include varied antibodies directed against different determinants (epitopes) of an antigen, whereas monoclonal antibodies are directed against a single determinant on the antigen. The term "monoclonal", in describing antibodies, indicates the character of the antibody as being obtained from a substantially homogeneous population of antibodies, and is not to be construed as requiring production of the antibody by any particular method. For example, monoclonal antibodies used in the present invention can be produced using conventional hybridoma technology first described by Kohler et al., Nature 256:495 (1975), or they can be made using recombinant DNA methods (see, e.g., U.S. Pat. No. 4,816,567). Monoclonal antibodies can also be isolated from phage antibody libraries, e.g., using the techniques described in Clackson et al., Nature 352:624-628 (1991); Marks et al., J. Mol. Biol. 222:581-597 (1991); and U.S. Pat. Nos. 5,223,409; 5,403,484; 5,571,698; 5,427,908 5,580,717; 5,969,108; 6,172,197; 5,885,793; 6,521,404; 6,544,731; 6,555,313; 6,582,915; and 6,593,081).

The monoclonal antibodies described herein include "chimeric" and "humanized" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). "Humanized" forms of non-human (e.g., murine) antibodies are chimeric antibodies which contain minimal sequence derived from non-human immunoglobulin. For the most part, humanized antibodies are human immunoglobulins (recipient antibody) in which the hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

The monoclonal antibodies described herein also include "human" antibodies, which can be isolated from various sources, including, e.g., from the blood of a human patient or recombinantly prepared using transgenic animals. Examples of such transgenic animals include KM-Mouse® (Medarex, Inc., Princeton, N.J.) which has a human heavy chain transgene and a human light chain transchromosome (see WO 02/43478), Xenomouse® (Abgenix, Inc., Fremont Calif.; described in, e.g., U.S. Pat. Nos. 5,939,598; 6,075,181; 6,114, 598; 6,150,584 and 6,162,963 to Kucherlapati et al.), and HuMAb-Mouse® (Medarex, Inc.; described in, e.g., Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, U.S. Pat. Nos. 5,545,806; 5,569, 825; 5,625,126; 5,633,425; 5,789,650; 5,877,397; 5,661,016; 5,814,318; 5,874,299; and 5,770,429; 5,545,807; and PCT Publication Nos. WO 92/03918, WO 93/12227, WO 94/25585, WO 97/13852, WO 98/24884 and WO 99/45962, WO 01/14424 to Korman et al.). Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The term "hypervariable region" is used to describe the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (113) in the heavy chain variable domain; see Kabat et al., Sequences of Proteins of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues.

As used herein, the term "immunoadhesin" designates antibody-like molecules which combine the "binding domain" of a heterologous "adhesin" protein (e.g. a receptor, ligand or enzyme) with the effector functions of an immunoglobulin constant domain. Structurally, an immunoadhesin comprises a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin is preferably derived from γ1, γ2, or γ4 heavy chains, since immunoadhesins comprising these regions can be purified by Protein A chromatography (Lindmark et al., J. Immunol. Meth. 62:1-13 (1983)). Immunoadhesins can be purified according to methods of the present invention.

The term "ligand binding domain" refers to any native cell-surface receptor or any region or derivative thereof retaining at least a qualitative ligand binding of a corresponding native receptor. In a specific embodiment, the receptor is from a cell-surface polypeptide having an extracellular domain which is homologous to a member of the immunoglobulin super gene family. Other receptors, which are not members of the immunoglobulin super gene family but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

An "antibody-immunoadhesin chimera" comprises a molecule which combines at least one binding domain of an antibody (as herein defined) with at least one immunoadhesin (as defined in this application). Exemplary antibody-immunoadhesin chimeras are the bispecific CD4-IgG chimeras described in Berg et al., PNAS (USA) 88:4723-4727 (1991) and Chamow et al., J. Immunol. 153:4268 (1994).

As used herein, a "mixture" comprises a polypeptide of interest (for which purification is desired) and one or more contaminant, i.e., impurities. The mixture can be obtained directly from a host cell or organism producing the polypeptide. Without intending to be limiting, examples of mixtures that can be purified according to a method of the present invention include harvested cell culture fluid, cell culture supernatant and conditioned cell culture supernatant. A mixture that has been "partially purified" has already been subjected to a chromatography step, e.g., non-affinity chromatography, affinity chromatography, etc. A "conditioned mixture" is a mixture, e.g., a cell culture supernatant that has been prepared for a chromatography step used in a method of the invention by subjecting the mixture to one or more of buffer exchange, dilution, salt addition, pH titration or filtration in order to set the pH and/or conductivity range and/or buffer matrix to achieve a desired chromatography performance. A "conditioned mixture" can be used to standardize loading conditions onto the first chromatography column. In general, a mixture can be obtained through various separation means well known in the art, e.g., by physically separating dead and viable cells from other components in the broth at the end of a bioreactor run using filtration or centrifugation, or by concentration and/or diafiltration of the cell culture supernatant into specific ranges of pH, conductivity and buffer species concentration.

The terms "impurity" and "contaminant", and grammatical variations thereof, are used interchangeably to mean any material, other than the protein of interest for which it is desirable to have removed from a composition containing the protein of interest. Contaminants include, but are not limited to, any biological macromolecule such as host cell proteins (e.g., CHOPs), polypeptides other than the protein of interest, nucleic acids (e.g., DNA and RNA), lipids, saccharides, endotoxins, bacteria or other microorganisms such as yeast, media components, and any molecule that is part of an adsorbent used in chromatography which may leach into a sample during chromatography, and the like.

The term "protein of interest" and "target protein" are used interchangeably to refer to a protein, as described above, e.g., an antibody, for which it is desirable to purify from a mixture according to a method of the present invention.

The term "host cell protein", or "HCP", refers to any of the proteins derived from the metabolism (intra and extra-cellular) of the host cell that expresses the target protein, including any proteins expressed from the genome of the host cell or proteins that are recombinantly expressed, and which are not considered the target protein. The host cell can be any cell that is capable of expressing the target protein, particularly mammalian (e.g., CHO and murine myeloma cell lines such as NSO), insect bacterial, plant and yeast cell lines. In a particular embodiment of the invention, the HCP is a "Chinese hamster ovary cell protein", or "CHOP", which refers to any of the host cell proteins ("HCP") derived from a Chinese hamster ovary ("CHO") cell culture. The HCP is present generally as an impurity in a cell culture medium or lysate [(e.g., a harvested cell culture fluid ("HCCF")], which contains the protein of interest. The amount of HCP present in a mixture comprising a protein of interest provides a measure of the degree of purity for the protein of interest. Typically, the amount of HCP in a protein mixture is expressed in parts per million relative to the amount of the protein of interest in the mixture.

The term "parts per million" or "ppm" are used interchangeably herein to refer to a measure of purity of the protein of interest purified by a method of the invention. The units ppm refer to the amount of HCP in nanograms/milliliter per protein of interest in milligrams/milliliter, where the proteins are in solution [i.e., as described in an Example infra, HCP ppm=(CHOP ng/ml)/(protein of interest mg/ml)]. Where the proteins are dried, such as by lyophilization, ppm refers to (HCP ng)/(protein of interest mg).

The term "purify", and grammatical variations thereof, is used to mean the removal, whether completely or partially, of at least one impurity from a mixture containing the polypeptide and one or more impurities, which thereby improves the level of purity of the polypeptide in the composition (i.e., by decreasing the amount (ppm) of impurity(ies) in the composition). According to the present invention, purification is performed with two non-affinity chromatography steps and no in-process TFF steps. A method of the present invention can purify the protein of interest to achieve a composition which contains less than 100 ppm HCP and preferably less than 90 ppm, less than 80 ppm, less than 70 ppm, less than 60 ppm, less than 50 ppm, less than 40 ppm, less than 30 ppm, less than 20 ppm, less than 10 ppm, or less than 5 ppm HCP, as determined by ELISA.

As used herein, the term "isolate", and grammatical variations thereof, refers to the separation of a purified protein of interest from additional substances, e.g., from a column or resin used to purify the protein of interest, in order to achieve a homogenous composition, which contains the protein of interest substantially free from contaminants, impurities and other substances.

The term "chromatography" refers to the process by which a solute of interest, e.g., a protein of interest, in a mixture is separated from other solutes in the mixture by percolation of the mixture through an adsorbent, which adsorbs or retains a solute more or less strongly due to properties of the solute, such as pI, hydrophobicity, size and structure, under particular buffering conditions of the process.

An "adsorbent" is any solid and fixed substance capable of adsorbing another substance to its surface by adhesion by either direct interaction with the molecule of interest or interaction with compounds that are attached to the adsorbent. Adsorbents that are useful in various types of chromatography are well known in the art and are readily available through commercial sources.

The term "affinity chromatography" and "protein affinity chromatography" are used interchangeably to refer to a protein separation technique in which a protein of interest is reversibly and specifically bound to a biospecific ligand, usually as a combination of spatial complementarity and one or more types of chemical interactions, e.g., electrostatic forces, hydrogen bonding, hydrophobic forces, and/or van der Waals forces at the binding site. These interactions are not due to the general properties of the molecule such as isoelectric point, hydrophobicity or size but are a result of specific interactions from the molecule of interest and the ligand such as the hydrophobic and precise protein domain fit for protein A and antibody interactions, for example. Protein A is an example of an adsorbent, which can be fixed to a solid support, e.g., Sepharose, for binding molecules that contain an $F_C$ region. See Ostrove (1990) in Guide to Protein Purification, Methods of Enzymology 182: 357-379, which is incorporated herein by reference in its entirety.

Any ligand can be used to purify its respective specific binding protein. Preferably, the biospecific ligand is covalently attached to a chromatographic solid phase material and is accessible to the protein of interest (e.g. antibody, enzyme, or receptor protein) in solution as the solution contacts the chromatographic solid phase material. The protein of interest retains its specific binding affinity for the biospecific ligand (antigen, substrate, cofactor, or hormone, for example) during the chromatographic steps, while other solutes and/or proteins in the mixture do not bind appreciably or specifically to the ligand. Binding of the protein of interest to the immobilized ligand allows contaminating proteins or protein impurities to be passed through the chromatographic medium while the protein of interest remains specifically bound to the immobilized ligand on the solid phase material. The specifically bound protein is then removed form the immobilized ligand with low pH, high pH, low salt, high salt, competing ligand, or the like, and passes through the chromatographic column with the elution buffer. Contaminating proteins having a lower relative concentration to the protein of interest, and other types of contaminants such as nucleic acids and endotoxin, that were earlier allowed to pass through the column, may also be present.

The terms "specific binding" and "binding specificity", and grammatical variations thereof, describe the generally specific and reversible interactions between a protein of interest and a ligand requiring the combined effects of spatial complementarity of protein and ligand structures at a binding site coupled with one or more type of electrostatic forces, hydrogen bonding, hydrophobic forces, and/or van der Waals forces at the binding site. The ligand should have chemically modifiable groups which allow it to be attached to the matrix without destroying its binding activity. The ligand should ideally have an affinity for the binding substance in the range $10^{-4}$ to $10^{-8}$ M in free solution. The greater the spatial complementarity and the stronger the other forces at the binding site, the greater will be the binding specificity of a protein for its respective ligand. Non-limiting examples of specific binding include antibody-antigen binding, enzyme-substrate binding, enzyme-cofactor binding, metal ion chelation, DNA binding protein-DNA binding, regulatory protein-protein interactions, and the like.

The terms "non-affinity chromatography" and "non-affinity purification" refer to a purification step which does not use affinity chromatography but rather requires a non-specific binding interaction between a solute (e.g., protein of interest) and the adsorbent matrix.

The term "non-specific binding" as used herein, refers to the interactions between a protein of interest and a ligand or other compound bound to a solid phase matrix through non-specific interactions, e.g., through electrostatic forces, hydrogen bonding, hydrophobic forces, and/or van der Waals forces at an interaction site, but lacking the structural complementarity that enhances the effects of the non-structural forces such as in affinity (specific) binding. Examples of chromatography processes that rely on non-specific binding, rather than affinity, include ionic exchange chromatography (e.g., anionic and cationic exchange) and hydrophobic charge induction chromatography.

The term "hydrophobic charge induction chromatography" (or "HCIC") is a type of mixed mode chromatographic process in which the protein of interest in the mixture binds to a dual mode (i.e., there is one mode for binding and another mode for elution), ionizable ligand [see Boschetti et al., 2000, Genetic Engineering News 20(13)] through mild hydrophobic interactions in the absence of added salts (e.g. a lyotropic salts). A "hydrophobic charge induction chromatography resin" is a solid phase that contains a ligand which has the combined properties of thiophilic effect (i.e., utilizing the properties of thiophilic chromatography), hydrophobicity and an ionizable group for its separation capability. Thus, an HCIC resin used in a method of the invention contains a ligand that is ionizable and mildly hydrophobic at neutral (physiological) or slightly acidic pH, e.g., about pH 5 to 10, preferably about pH 6 to 9.5. At this pH range, the ligand is predominantly uncharged and binds a protein of interest via mild non-specific hydrophobic interaction. As pH is reduced, the ligand acquires charge and hydrophobic binding is disrupted by electrostatic charge repulsion towards the solute due to the pH shift.

Examples of suitable ligands for use in HCIC include any ionizable aromatic or heterocyclic structure (e.g. those having a pyridine structure, such as 2-aminomethylpyridine, 3-aminomethylpyridine and 4-aminomethylpyridine, 2-mercaptopyridine, 4-mercaptopyridine or 4-mercaptoethylpyridine, mercaptoacids, mercaptoalcohols, imidazolyl based, mercaptomethylimidazole, 2-mercaptobenzimidazole, aminomethylbenzimidazole, histamine, mercaptobenzimidazole, diethylaminopropylamine, aminopropylmorpholine, aminopropylimidazole, aminocaproic acid, nitrohydroxybenzoic acid, nitrotyrosine/ethanolamine, dichlorosalicylic acid, dibromotyramine, chlorohydroxyphenylacetic acid, hydroxyphenylacetic acid, tyramine, thiophenol, glutathione, bisulphate, and dyes, including derivatives thereof; see Burton and Harding, Journal of Chromatography A 814: 81-81 (1998) and Boschetti, Journal of Biochemical and Biophysical Methods 49: 361-389 (2001), which are hereby incorporated by reference in their entireties), which has an aliphatic chain and at least one sulfur atom on the linker arm and/or ligand structure. An example of an HCIC resin includes MEP HYPERCEL (Pall Corporation; East Hills, N.Y.).

The terms "ion-exchange" and "ion-exchange chromatography" refer to a chromatographic process in which an ionizable solute of interest (e.g., a protein of interest in a mixture) interacts with an oppositely charged ligand linked (e.g., by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange, anion exchange, and mixed mode chromatographies.

The phrase "ion exchange material" refers to a solid phase that is negatively charged (i.e. a cation exchange resin) or positively charged (i.e. an anion exchange resin). In one embodiment, the charge can be provided by attaching one or more charged ligands (or adsorbents) to the solid phase, e.g.

by covalent linking. Alternatively, or in addition, the charge can be an inherent property of the solid phase (e.g. as is the case for silica, which has an overall negative charge).

A "cation exchange resin" refers to a solid phase which is negatively charged, and which has free cations for exchange with cations in an aqueous solution passed over or through the solid phase. Any negatively charged ligand attached to the solid phase suitable to form the cation exchange resin can be used, e.g., a carboxylate, sulfonate and others as described below. Commercially available cation exchange resins include, but are not limited to, for example, those having a sulfonate based group (e.g., MonoS, MiniS, Source 15S and 30S, SP Sepharose Fast Flow™, SP Sepharose High Performance from GE Healthcare, Toyopearl SP-650S and SP-650M from Tosoh, Macro-Prep High S from BioRad, Ceramic HyperD S, Trisacryl M and LS SP and Spherodex LS SP from Pall Technologies,); a sulfoethyl based group (e.g., Fractogel SE, from EMD, Poros S-10 and S-20 from Applied Biosystems); a sulphopropyl based group (e.g., TSK Gel SP 5PW and SP-5PW-HR from Tosoh, Poros HS-20 and HS 50 from Applied Biosystems); a sulfoisobutyl based group (e.g., (Fractogel EMD $SO_3^-$ from EMD); a sulfoxyethyl based group (e.g., SE52, SE53 and Express-Ion S from Whatman), a carboxymethyl based group (e.g., CM Sepharose Fast Flow from GE Healthcare, Hydrocell CM from Biochrom Labs Inc., Macro-Prep CM from BioRad, Ceramic HyperD CM, Trisacryl M CM, Trisacryl LS CM, from Pall Technologies, Matrx Cellufine C500 and C200 from Millipore, CM52, CM32, CM23 and Express—Ion C from Whatman, Toyopearl CM-650S, CM-650M and CM-650C from Tosoh); sulfonic and carboxylic acid based groups (e.g. BAKERBOND Carboxy-Sulfon from J. T. Baker); a carboxylic acid based group (e.g., WP CBX from J. T Baker, DOWEX MAC-3 from Dow Liquid Separations, Amberlite Weak Cation Exchangers, DOWEX Weak Cation Exchanger, and Diaion Weak Cation Exchangers from Sigma-Aldrich and Fractogel EMD COO- from EMD); a sulfonic acid based group (e.g., Hydrocell SP from Biochrom Labs Inc., DOWEX Fine Mesh Strong Acid Cation Resin from Dow Liquid Separations, UNOsphere S, WP Sulfonic from J. T. Baker, Sartobind S membrane from Sartorius, Amberlite Strong Cation Exchangers, DOWEX Strong Cation and Diaion Strong Cation Exchanger from Sigma-Aldrich); and a orthophosphate based group (e.g., P11 from Whatman).

An "anion exchange resin" refers to a solid phase which is positively charged, thus having one or more positively charged ligands attached thereto. Any positively charged ligand attached to the solid phase suitable to form the anionic exchange resin can be used, such as quaternary amino groups Commercially available anion exchange resins include DEAE cellulose, Poros PI 20, PI 50, HQ 10, HQ 20, HQ 50, D 50 from Applied Biosystems, Sartobind Q from Sartorius, MonoQ, MiniQ, Source 15Q and 30Q, Q, DEAE and ANX Sepharose Fast Flow, Q Sepharose high Performance, QAE SEPHADEX™ and FAST Q SEPHAROSE™ (GE Healthcare), WP PEI, WP DEAM, WP QUAT from J. T. Baker, Hydrocell DEAE and Hydrocell QA from Biochrom Labs Inc., UNOsphere Q, Macro-Prep DEAE and Macro-Prep High Q from Biorad, Ceramic HyperD Q, ceramic HyperD DEAE, Trisacryl M and LS DEAE, Spherodex LS DEAE, QMA Spherosil LS, QMA Spherosil M and Mustang Q from Pall Technologies, DOWEX Fine Mesh Strong Base Type I and Type II Anion Resins and DOWEX MONOSPHER E 77, weak base anion from Dow Liquid Separations, Intercept Q membrane, Matrex Cellufine A200, A500, Q500, and Q800, from Millipore, Fractogel EMD TMAE, Fractogel EMD DEAE and Fractogel EMD DMAE from EMD, Amberlite weak strong anion exchangers type I and II, DOWEX weak and strong anion exchangers type I and II, Diaion weak and strong anion exchangers type I and II, Duolite from Sigma-Aldrich, TSK gel Q and DEAE 5PW and 5PW-HR, Toyopearl SuperQ-650S, 650M and 650C, QAE-550C and 650S, DEAE-650M and 650C from Tosoh, QA52, DE23, DE32, DE51, DE52, DE53, Express-Ion D and Express-Ion Q from Whatman.

A "mixed mode ion exchange resin" refers to a solid phase which is covalently modified with cationic, anionic, and/or hydrophobic moieties. Examples of mixed mode ion exchange resins include BAKERBOND ABX™ (J. T. Baker; Phillipsburg, N.J.), ceramic hydroxyapatite type I and II and fluoride hydroxyapatite (BioRad; Hercules, Calif.) and MEP and MBI HyperCel (Pall Corporation; East Hills, N.Y.).

The term "thiophilic" refers to the selectivity that proteins have for sulfone groups that lie in close proximity to thioether groups (Porath et al, 1985). "Thiophilic chromatography" also known as "thiophilic adsorption chromatography", is a type of non-affinity chromatography in which a protein of interest, which contains thiophilic regions and aromatic amino residues, bind to a sulphur containing ligand for the isolation of the protein. A thiophilic gel can be prepared by reducing divinylsulfone(coupled to Sepharose 4B) with β-mercaptoethanol. Thiophilic adsorption chromatography is based on electron donor-acceptor properties and is distinct from chromatography based on hydrophobicity. Hydrophobic associations and ionic interactions do not occur with thiophilic sorbents since thio-ethylsulfone structures do not possess pronounced hydrophobicity or ionic charges. Examples of commercially available thiophilic chromatography resins include Fractogel EMD TA (Merck; Rahway, N.J.), Uniflow and Superflow resin (Clontech) and T-Gel (Pierce).

The term "solid phase" is used to mean any non-aqueous matrix to which one or more ligands can adhere or alternatively, in the case of size exclusion chromatography, it can refer to the gel structure of a resin. The solid phase can be any matrix capable of adhering ligands in this manner, e.g., a purification column, a discontinuous phase of discrete particles, a membrane, filter, gel, etc. Examples of materials that can be used to form the solid phase include polysaccharides (such as agarose and cellulose) and other mechanically stable matrices such as silica (e.g. controlled pore glass), poly(styrenedivinyl)benzene, polyacrylamide, ceramic particles and derivatives of any of these. The present invention is not limited to any particular solid phase material for use in a chromatography step, and those having ordinary skill in the art will be able to select appropriate solid phase material for use in the present invention.

The term "detergent" refers to ionic, zwitterionic and nonionic surfactants, which are useful for preventing aggregation of proteins and to prevent non-specific interaction or binding of contaminants to the protein of interest, and can be present in various buffers used in the present invention, including sanitization, equilibration, loading, post-load wash(es), elution or strip buffers. In particular embodiments, a detergent is added to a wash buffer. Examples of detergents that can be used in the invention include, but are not limited to polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; MONAQUAT™ series (Mona Industries, Inc., Paterson, N.J.); Igepal CA-630, Pluronic, Triton, BRIJ, Atlas G2127, Genapol, HECAMEG, LUBROL PX, MEGA, NP, THESIT, TOPPS, CHAPS, CHAPSO, DDMAU, EMPIGEN BB, AWITTERGENT and C12E8. The detergent can be added in any working buffer and can also be included in the feed containing the molecule of interest. Detergents can be present in any amount suitable for use in a protein purification process, e.g., from about 0.001% to about 20% and typically from about 0.01% to about 1%. In a particular embodiment, polysorbate 80 is used in a wash buffer for CEXC.

A "buffer" used in the present invention is a solution that resists changes in pH by the addition of acid or base by the action of its acid-base conjugates components. Various buffers can be employed in a method of the present invention depending on the desired pH of the buffer and the particular step in the purification process [see Buffers. A Guide for the Preparation and Use of Buffers in Biological Systems, Gueffroy, D., ed. Calbiochem Corporation (1975)]. Non-limiting examples of buffer components that can be used to control the pH range desirable for a method of the invention include acetate, citrate, histidine, phosphate, ammonium buffers such as ammonium acetate, succinate, MES, CHAPS, MOPS, MOPSO, HEPES, Tris, and the like, as well as combinations of these TRIS-malic acid-NaOH, maleate, chloroacetate, formate, benzoate, propionate, pyridine, piperazine, ADA, PIPES, ACES, BES, TES, tricine, bicine, TAPS, ethanolamine, CHES, CAPS, methylamine, piperidine, 0-boric acid, carbonic acid, lactic acid, butaneandioic acid, diethylmalonic acid, glycylglycine, HEPPS, HEPPSO, imidazole, phenol, POPSO, succinate, TAPS, amine-based, benzylamine, trimethyl or dimethyl or ethyl or phenyl amine, ethylenediamine, or mopholine Additional components (additives) can be present in a buffer as needed, e.g., salts can be used to adjust buffer ionic strength, such as sodium chloride, sodium sulfate and potassium chloride; and other additives such as amino acids (such as glycine and histidine), chaotropes (such as urea), alcohols (such as ethanol, mannitol, glycerol, and benzyl alcohol), detergents (see supra.), and sugars (such as sucrose, mannitol, maltose, trehalose, glucose, and fructose). The buffer components and additives, and the concentrations used, can vary according to the type of chromatography practiced in the invention.

The pH and conductivity of the buffers can vary depending on which step in the purification process the buffer is used. In CEXC the pH of the buffer can be between 3 and 10, more preferably from about pH 4.0 to 8.0; conductivity can be from about 0.1 to 40 mS/cm, more preferably from about conductivity 0.5 to 15 mS/cm, depending on the purification step and the buffer employed. In HCIC the pH of the buffers can be from about 3 to 10, more preferably from about pH 4.0 to 9.0; conductivity can be from about 0.0 (WFI; water for injection) to 90.0 mS/cm, more preferably from about 0.1 to 9.0 mS/cm, depending on the purification step and the buffer employed. Buffers used throughout the purification process are described in greater detail below for each chromatography step.

A "sanitization" solution is typically used to clean the resin by removing any bound contaminants, e.g., those of biological origin, prior to the purification process. Any desirable buffer could be used for this purpose provided it is compatible with the particular column and resin selected according to a method of the invention. Preferably, the pH of the sanitization solution is high, e.g., pH 10 or greater, more preferably pH 11 or greater, and still more preferably pH 12 or greater; alternatively, the pH of the sanitization solution can be low, e.g. pH 4 or less, more preferably pH 3 or less. In a particular embodiment, the HCIC and CEXC columns are cleaned using a sanitization solution that includes 1N NaOH, pH≧12.

An "equilibration buffer" is used to adjust the pH and conductivity of the chromatography column prior to loading the column with the mixture containing the protein of interest for purification. Suitable buffers that can be used for this purpose are well known in the art, e.g., such as buffers described above, and include any buffer at pH that is compatible with the selected resin used in the chromatography step for purifying the protein of interest. This buffer is used to load the mixture comprising the polypeptide of interest. The equilibration buffer has a conductivity and/or pH such that the polypeptide of interest is bound to the resin or such that the protein of interest flows through the column while one or more impurities bind to the column. In a preferred embodiment, equilibration of the chromatography column is completed when the pH and conductivity are within ±0.2 and ±0.4 mS/cm of the equilibrating buffer, respectively, more preferably within ±0.1 and ±0.2 mS/cm of the equilibrating buffer, respectively. In preferred embodiments, the equilibration buffer species for CEXC and HCIC are sodium phosphate based. In CEXC the pH of the equilibration buffer is from about 3 to about 9, more preferably pH from about 4.0 to 8.0, conductivity from about 0.1 to about 40 mS/cm, more preferably from about 0.5 to 10.0 mS/cm. In HCIC the pH of the equilibration buffer is from about 5 to about 10, more preferably pH from about 6 to 9, conductivity from about 0.0 (WFI) to about 90 mS/cm, more preferably conductivity from about 2.0 to 9 mS/cm.

A "loading buffer" is used to load the mixture containing the protein of interest onto the column. Any appropriate solution can be used as the loading buffer. The conductivity and pH of the loading buffer in the present process is selected such that the protein of interest is bound to the resin while contaminants are able to flow through the column. Preferably, the loading buffer can be buffer exchanged. The loading buffer can also be prepared from a buffered mixture derived from a previous purification step, such as the elution buffer. Suitable buffers for use as a loading buffer with the selected resin are well known in the art, e.g., such as those described above. It shall be appreciated by those having ordinary skill in the art that loading buffers for CEXC and HCIC can be used at comparable (if not the same) pH and conductivities as described above for the equilibration buffers for CEXC and HCIC.

The terms "wash buffer" or "post load wash", as used herein, refer to a buffer used to elute one or more impurities from the ion exchange resin prior to eluting the protein of interest. The term "washing", and grammatical variations thereof, is used to describe the passing of an appropriate wash buffer through or over the chromatography resin. Conveniently, the wash, equilibration and loading buffers can be the same, but this is not required. The pH and conductivity of the buffer is such that one or more impurities are eluted from the resin while the resin retains the polypeptide of interest. If desirable, the wash buffer may contain a detergent, as described above, such as a polysorbate. Any suitable buffer at a pH compatible with the selected resin can be used for purifying the protein of interest, such as the buffers described above. Selection of pH and conductivity of the wash buffer are important for removal of HCPs and other contaminants without significantly eluting the protein of interest. The conductivity and pH can be reduced, or maintained or increased in wash buffers used in subsequent wash steps for the HCIC and CEXC chromatography after loading the mixture in order to remove more hydrophilic and more acidic or basic contaminants than that of the protein of interest and to reduce the conductivity of the system prior to the elution step. In a particular embodiment, only the conductivity is decreased for the HCIC chromatography, and post-load washes for CEXC do not include any change in either pH or conductivity of the buffers used for equilibration, load and post-load wash.

In a particular embodiment the wash buffer used for CEXC is sodium phosphate. The pH of a wash buffer used in CEXC can be from about 3 to about 9, more preferably pH from about 4.0 to about 8.0; and conductivity from about 0.1 to about 40 mS/cm, more preferably conductivity from about 0.5 to about 10 mS/cm.

The wash buffer used in HCIC can be any suitable buffer to achieve a desirable pH and conductivity, and can be selected from a buffer as described above. In a particular embodiment, the wash buffer used in HCIC is sodium phosphate. The pH of a wash buffer used in HCIC can be from about 5 to about 10, more preferably pH from about 6 to about 9; and conductivity from about 0.0 (WFI) to about 90 mS/cm, more preferably conductivity from about 0.1 to about 9 mS/cm.

The term "elution buffer", as used herein, refers to a buffer used to elute the protein of interest from the solid phase (i.e, chromatography resin). The term "elute", and grammatical variations thereof, refers to the removal of a molecule, e.g., polypeptide of interest, from a chromatography material by using appropriate conditions, e.g., altering the ionic strength or pH of the buffer surrounding the chromatography material, by addition of a competitive molecule for the ligand, by altering the hydrophobicity of the molecule or by changing a chemical property of the ligand (e.g. charge), such that the protein of interest is unable to bind the resin and is therefore eluted from the chromatography column. The term "eluate" refers to the effluent off the column containing the polypeptide of interest when the elution is applied onto the column. After elution of the polypeptide of interest the column can be regenerated, sanitized and stored as needed.

The pH and conductivity of the elution buffer are selected such that the protein of interest is eluted from the particular CEXC or HCIC resin used in the process. Buffers suitable for use as an elution buffer are described above. In a particular embodiment, the elution buffer used in CEXC and HCIC chromatographies is sodium phosphate and sodium acetate, respectively.

The pH of the elution buffer used in CEXC can be from about 3.0 to about 10, more preferably pH from about 4 to about 8; and conductivity from about 0.1 to about 40 mS/cm, more preferably conductivity from about 5 to about 15 mS/cm.

The pH of the elution buffer used in HCIC can be from about 3.0 to about 7.0, more preferably pH from about 4.0 to about 6.0; and conductivity from about 0.0 (WFI) to about 20 mS/cm, more preferably conductivity from about 0.1 to about 2 mS/cm.

If desired, additional solutions may be used to prepare the column for reuse. For example, a "regeneration solution" can be used to "strip" or remove tightly bound contaminants from a column used in the purification process. Typically, the regeneration solution has a conductivity and pH sufficient to remove substantially any remaining impurities and protein of interest from the resin.

As used herein, the term "conductivity" refers to the ability of an aqueous solution to conduct an electric current between two electrodes at a particular temperature. A current flows by ion transport in solution. Therefore, with an increasing amount of ions present in the aqueous solution, the solution will have a higher conductivity. In a method of the present invention the temperature at which purification is typically performed can be from about 4 to about 37° C., more preferably from about 15 to about 25° C. within the specified pH ranges.

The unit of measurement for conductivity is milliSiemens per centimeter (mS/cm), and can be measured using a standard conductivity meter. The conductivity of a solution can be altered by changing the concentration of ions therein. For example, the concentration of a buffering agent and/or concentration of a salt (e.g. NaCl or KCl) in the solution may be altered in order to achieve the desired conductivity. Preferably, the salt concentration is modified to achieve the desired conductivity as described in the Example below.

The "pI" or "isoelectric point" of a polypeptide refers to the pH at which the polypeptide's positive charge balances its negative charge. The pI can be calculated according to various conventional methodologies, e.g., from the net charge of the amino acid and/or sialic acid residues on the polypeptide or by using isoelectric focusing.

As used herein, a "low pH hold" refers to a decrease in the pH of an eluate which contains the protein of interest, where the pH decrease is to less than about pH 5.0, preferably less than about pH 4.0, more preferably less than about pH 3.7, and most preferably about pH 3.4 to about 3.6 in order to achieve viral inactivation (i.e., at least a 2 log reduction in viral titer, more preferably at least a 3 log reduction) followed by an increase in pH in order to prepare the eluate for the second chromatography step or to bring the product to a matrix that provides stability to the molecular integrity of the product of interest. Any suitable acid can be applied to the eluate containing the protein of interest to decrease the pH for the low pH hold, e.g., 1 N HCl or glacial acetic acid. Any suitable base can be applied to the eluate to return its pH to more neutral ranges, e.g., 1N NaOH or 1N Tris. The low pH hold typically results in an increase in conductivity of at least 0.5 mS/cm. If the low pH hold takes place after the first chromatography step and the second chromatography step is cationic exchange chromatography then it is likely that the increase in pH will be to within a suitable pH range, which is about 3.0 to about 9.0, preferably about 4.0-8.0. If the low pH hold takes place after the first chromatography step and the second chromatography step is HCIC then the increase in pH will likely be within a pH range suitable for HCIC, which is about pH 5 to about pH 10.0, preferably about pH 6.0 to about 9.0. The low pH hold can also take place after the second chromatography but in the method of invention has been chosen to take place in between chromatography steps due to experimental convenience. It shall be appreciated by those having ordinary skill in the art that a low pH hold step is not essential to achieve levels of purity attainable by a method of the present invention.

"Tangential flow filtration" or "TFF" or "crossflow filtration" refers to a filtration process in which the sample mixture circulates across the top of a membrane, while applied pressure causes certain solutes and small molecules to pass through the membrane. In TFF, typically, the solution flows parallel to the filter membrane. A pressure differential across the membrane causes fluid and filterable solutes (whose molecular weight is smaller than that of the membranes or behaves like so, such as globular proteins) to flow through the filter. This can be conducted as a continuous-flow process, since the solution is passed repeatedly over the membrane while the fluid that passes through the filter is continually drawn off into a separate circuit. In HPTFF (high performance tangential flow filtration) the membrane is charged, therefore using both size and charge of molecules to separate contaminants (see US Patent Pub. No. 2003/0229212). If desirable, TFF can be used to exchange the buffer in which the protein of interest is solubilized into another buffer that is more suitable for binding onto the chromatography resin prior to beginning a method of the present invention. In other words, TFF can be used before the first chromatography step, however, an in-process TFF step (i.e., the TFF occurs between the two chromatography steps) is unnecessary since the buffers and resins used in the present method permit direct movement from one resin to the next.

As used herein, "in-process" refers to any methodology, step, operation, etc. that is performed after commencing the load step for the first chromatography column, but prior to collection of the elution peak of the second chromatography column in a method of the present invention. An in-process methodology can directly result in a change in purity (such as an in-process TFF) or it does not directly result in a change in purity (such as a pH and/or conductivity adjustment where the result of the adjustment does not directly cause any change in purity).

It may be desirable to achieve a therapeutic grade protein purity using a method of the invention, in which case additional steps well-known in the art can be optionally employed to achieve a viral clearance capacity for both adventitious and endogenous viruses, e.g., low pH inactivation and viral filtration methods (including specific charged membrane filtration for viruses such as VR CUNO (CUNO) or DV20 (Pall Technologies), which are further described below.

As used herein "depth filtration" is a filtration method that uses depth filters, which are typically characterized by their design to retain particles within a filter matrix. The depth filter's capacity is typically defined by the depth, e.g. 10" or 20" of the matrix and thus the holding capacity for solids. In a method of the present invention a depth filter can be used to improve the viral clearance capacity of the purification scheme, however it is an optional step and not required to achieve purity levels of a method of the present invention. The depth filter for virus removal can be used at any point during the purification scheme, but is preferably used after the first chromatography step with low process volumes, due to the cost of the filter.

Description of the Process

In the method of the present invention CEXC and HCIC can be used in any order to purify a protein of interest to as little as about 100 ppm HCP or less and as high as 99% monomer purity or greater. Additional chromatography steps are not needed to obtain this high level of purity.

The protein of interest can be produced by living host cells that have been genetically engineered to produce the protein. Methods of genetically engineering cells to produce proteins are well known in the art. See e.g. Ausabel et al., eds. (1990), Current Protocols in Molecular Biology (Wiley, New York) and U.S. Pat. Nos. 5,534,615 and 4,816,567, each of which are specifically incorporated herein by reference. Such methods include introducing nucleic acids that encode and allow expression of the protein into living host cells. These host cells can be bacterial cells, fungal cells, or, preferably, animal cells grown in culture. Bacterial host cells include, but are not limited to E. coli cells. Examples of suitable E. coli strains include: HB101, DH5a, GM2929, JM109, KW251, NM538, NM539, and any E. coli strain that fails to cleave foreign DNA. Fungal host cells that can be used include, but are not limited to, Saccharomyces cerevisiae, Pichia pastoris and Aspergillus cells. A few examples of animal cell lines that can be used are CHO, VERO, DXB11, BHK, HeLa, Cos, MDCK, 293, 3T3, NS0 and WI138. New animal cell lines can be established using methods well know by those skilled in the art (e.g., by transformation, viral infection, and/or selection).

In particular embodiments, the protein of interest is produced in a CHO cell (see, e.g., WO 94/11026). Various types of CHO cells are known in the art, e.g., CHO-K1, CHO-DG44, CHO-DXB11, CHO/dhfr$^-$ and CHO—S.

Preparation of a Mixture for Protein Purification from Cellular Debris Initially depends on the manner of expression of the protein. Some proteins are caused to be secreted directly from the cell into the surrounding growth media, while other proteins are retained intracellularly. For such proteins produced intracellularly, the cell can be disrupted using any of a variety of methods, such as mechanical shear, osmotic shock, and enzymatic treatment. The disruption releases the entire contents of the cell into the homogenate, and in addition produces subcellular fragments which can be removed by centrifugation or by filtration. A similar problem arises, although to a lesser extent, with directly secreted proteins due to the natural death of cells and release of intracellular host cell proteins during the course of the protein production run.

When using recombinant techniques, the protein of interest can be produced intracellularly, in the periplasmic space, or directly secreted into the medium. A method of the invention does not rely on any particular methodology to remove cellular debris. Any method can be employed by the skilled practitioner to accomplish this. If the protein is produced intracellularly, as a first step, the particulate debris, either host cells or lysed fragments, can be removed, for example, by a centrifugation or filtration step in order to prepare a mixture for purification. If the protein is secreted into the medium, the recombinant host cells may be separated from the cell culture medium by, e.g., tangential flow filtration (TFF) or depth filtration, in order to prepare a mixture for purification.

Figure 1:
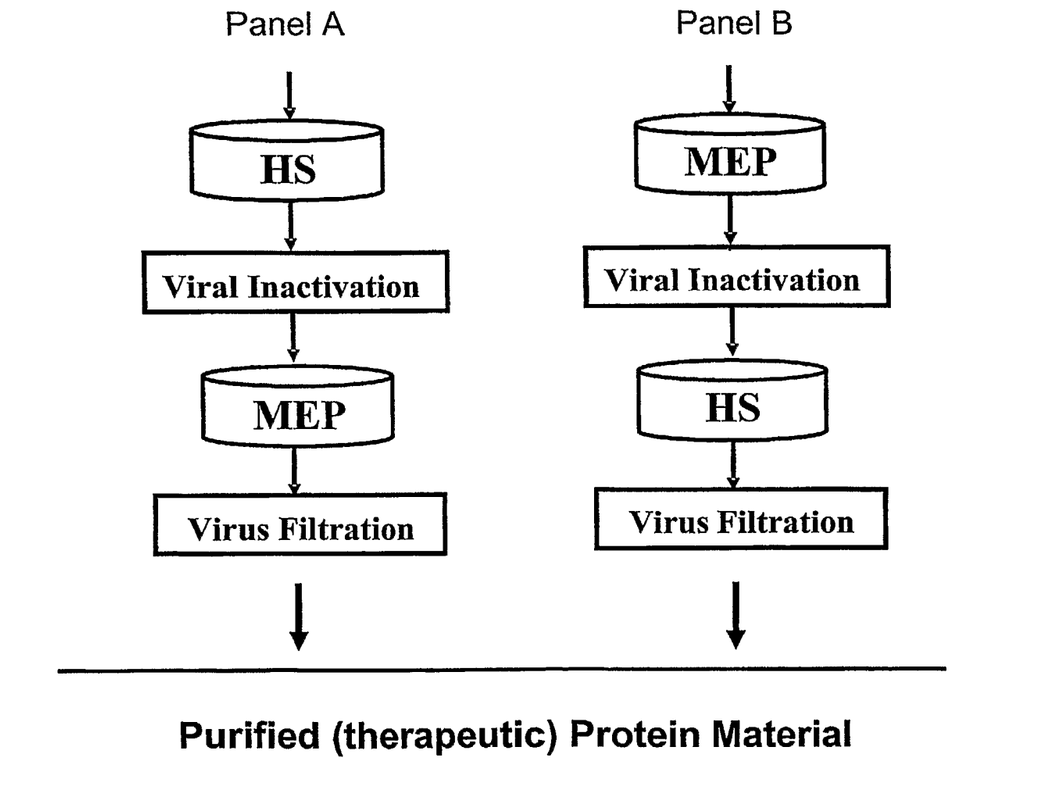
FIG. 1 shows a flow diagram of a two-step purification process of the invention, where Panel A and Panel B refer to the same resins used in different sequential order. Panel A represents a first embodiment of the purification process of the invention, where cation exchange chromatography (CEXC) is the capture chromatography step followed by hydrophobic charge induction chromatography (HCIC) with only a pH manipulation in between the two chromatography steps. Panel B represents a second embodiment, where HCIC is the capture chromatography step followed by CEXC with only a pH manipulation in between the two chromatography steps. The approximate binding pH during capture was 6.2 for Panel A and 7.0 for Panel B.

According to the present invention, once a mixture containing the protein of interest has been obtained, its separation from contaminants in the mixture is performed using a combination of HCIC and CEXC chromatographies in either order as desired (see FIG. 1), under appropriate conditions, as described hereinabove. No other in-process purification steps, e.g., TFF or HPTFF, are required to achieve levels of purity attainable by a method of the present invention. Only pH manipulations are performed as needed between the two chromatography steps in order to prepare the mixture for purification in the second step of chromatography.

In a particular embodiment, the HCIC resin used is MEP HyperCel (Pall Corp.) and the CEXC resin is Poros 50HS (Applied Biosystems). These chromatography techniques separate mixtures of proteins on the basis of various properties, including charge and hydrophobicity. In essence, these separation methods cause proteins and other molecules to move at different rates down a long column in order to achieve a physical separation as the material passes further down the column. Under appropriate conditions as described hereinabove, the chromatography steps permit the protein of interest to adhere to the column, while allowing other material to pass through the column. The protein of interest is then differentially eluted by appropriate buffer. Alternatively, under appropriate conditions, the desired protein can be separated from impurities by adhering the impurities to the column, while the protein of interest passes through the column, i.e., the protein of interest is present in the "flow-through."

It shall be appreciated by those of ordinary skill in the art that a low pH hold can be incorporated into the present method if desirable. Due to viral clearance requirements of regulatory agencies for the production of therapeutic proteins, there must be at least two separate steps for viral inactivation and clearance, based on different chemical modes of action which are typically a low pH hold and a viral filtration step. The low pH hold typically employs pH shifts of the purified sample (e.g., see Example, infra.), and can be incorporated into the pH manipulation necessary to prepare for the second chromatography step. It shall be appreciated by those of ordinary skill in the art that a pH hold between the two chromatography steps can be accomplished using any methodology known in the art to accomplish the viral clearance typically achieved by a low pH hold, provided that the mixture containing the protein of interest is buffered appropriately prior to application on the second column.

For example, without intending to be limiting, a low pH hold following HCIC can be accomplished by using 1N HCl or glacial acetic acid to decrease the pH of the HCIC eluate to a pH range of about 3.4 to 3.6 followed by 2M Tris pH 9.0 to increase the pH to of the eluate to about 6.2; alternatively, following CEXC, 1N HCl or glacial acetic acid can be used to decrease the pH of the CEXC eluate to a pH range of about 3.4 to 3.6 and 2M Tris pH 9.0 to increase the pH of the eluate to about 7.0. A pH hold will typically result in an increase of at least 0.5 mS/cm in conductivity.

One of ordinary skill in the art will appreciate timing conditions for a low pH hold step used in a method of the present invention. Typically, a low pH hold is performed for at least about 30 minutes, preferably about 45 minutes, more preferably up to about 60 minutes, and most preferably up to about 90 minutes. In certain purification schemes it may be desirable to perform a low pH hold for up to 5 hours depending on the protein being purified If therapeutic grade protein formulation is desirable, then a second viral clearance step can be employed, e.g., a virus filtration step, which is, however, not required to achieve the levels of purity attainable by a method of the invention. Filtration devices that can be used in a method of the invention are well-known in the art (e.g., Ultipor® VF Grade DV20 or DV50 and Filtron® TFF (Pall Corporation, East Hills, N.Y.); Viresolve (Millipore, Billerica, Mass.); VR CUNO (CUNO; Meriden, Conn.); and Planova® (Asahi Kasei Pharma, Planova Division, Buffalo Grove, Ill.), in order to remove viruses and other biological materials, preferably with pore sizes smaller than 20 nm, which can remove polioviruses.

The chromatographic steps of the invention can be carried out by any mechanical means. Chromatography may be carried out in a column. The column may be run with or without pressure and from top to bottom or bottom to top. The direction of the flow of fluid in the column may be reversed during the chromatography process. Chromatography may also be carried out using a batch process in which the solid support is separated from the liquid used to load, wash, and elute the sample by any suitable means, including gravity, centrifugation, or filtration. Chromatography may also be carried out by contacting the sample with a charged filter that absorbs or retains some molecules in the sample more strongly than others, using the same chemical principles as those described for a chromatography resin. Although steps in the preparation of columns used in the present invention can be tailored to suit the individual needs of the practitioner, the following description is provided as guidance, and those having ordinary skill in the art will appreciate alterations can be made without departing from the spirit of the invention. Columns are prepared according to the manufacturer's instructions. Prior to purification, columns are typically sanitized using a sanitization solution, then charged using a lyotropic salt, e.g., 1 M NaCl, and equilibrated using an equilibration buffer. During the sanitization step, typically there is a hold, e.g., for about 30 minutes, preferably for about 1 hour, after the sanitization solution is applied onto the column in order to clean the resin having any bound contaminants, including contaminants of biological origin. The charge step neutralizes the resin by displacing the sanitization solution, e.g., in CEXC, NaCl can be used to remove NaOH from the column and maintain the resin ligand in contact with positively charged ions. After the column is charged, an equilibration buffer is used to equilibrate the column in order to prepare the pH and conductivity of the resin to bind the protein of interest. For example, the column can be considered equilibrated when its pH and conductivity are within ±0.1 and within ±0.2 mS/cm of the pH and conductivity of the equilibrating buffer, respectively.

A load mixture is prepared, which is typically a cell culture supernatant that is concentrated and buffer exchanged in an appropriate buffered salt (i.e. load buffer). The load mixture (i.e., containing the protein of interest for which purification is desired) derived from the recombinant host cells is loaded onto the equilibrated column (either CEXC or HCIC) using a loading buffer which optionally can be the same as the equilibration buffer. As the mixture flows through the solid phase of the column, the protein of interest and other impurities (e.g., HCPs if the protein is produced in a CHO cell) bind differentially to the solid phase, thereby permitting separation as the protein and contaminants pass through the chromatography column.

Once the mixture has been loaded onto the column and is bound to the resin, wash steps using a wash buffer as described are performed to clear contaminants from the column. Optionally, a first wash step can be performed at a slower flow rate than for the other wash and elution steps (but is not necessary), e.g., using a flow rate corresponding to several minutes (e.g., 5-10 minutes) residence time. Flow rates are discussed in greater detail infra. The pH and conductivity of the wash buffer are important during the first wash, particularly for HCIC chromatography, in order to maximize removal of HCPs. In the present method, the wash step in CEXC chromatography removes nucleic acids and remaining HCPs while retaining the protein of interest. The first wash step in HCIC chromatography removes HCPs while the second wash removes more hydrophilic contaminants, e.g., HCPs. HCIC is very efficient for nucleic acid removal because it mostly flows in the unbound fraction. If HCIC is employed as the first column, then a third wash step can be employed to further reduce levels of any hydrophilic contaminants.

To elute the protein of interest from the column, an appropriate elution buffer is used, as described above, to cause the protein of interest to reverse binding off the column. The type and concentration of buffer, salt, and/or other compound in the buffer composition are such that the buffer elutes impurity(ies) differentially in relation to the protein of interest, whereas the protein of interest is retained relative to the impurities. The appropriate pH and conductivity ranges for loading, wash, and elution buffers can be readily determined by those having ordinary skill in the art, using the Example provided herein as guidance, such that the protein of interest is recovered during elution. In order to minimize HCPs in the eluate containing the protein of interest, a reduced flow rate, described infra., can be employed, e.g., not greater than a corresponding residence time of 2 minutes, more preferably not greater that 3 minutes residence time, more preferably no greater than 10 minutes residence time. As the protein of interest is removed from the column, it is collected based on formation of a peak from rising $A_{280}$ to falling $A_{280}$ between 5 and 25% above baseline, as measured by absorbance. The baseline can be readily determined by one of ordinary skill in the art by measuring the absorbance of the equilibrating buffer at 250-280 nm while the buffer passes through the column. In order to reduce collection of HCPs to prepare a purified composition containing the protein of interest, it is preferred that eluate containing the protein of interest is collected before 25% of maximum peak height, since HCPs tend to elute at a later time or at lower pH values for the HCIC resin.

In essence, the separation methods used in the present invention cause contaminants to move at different rates down a long column, achieving a physical separation that increases as they pass further down the column, while the protein of interest adheres to the chromatography medium, and is then differentially eluted depending on the buffer. In the present purification method, the maximum rate at which a mixture moves down the column (HCIC or CEXC) is not greater than 30 minutes residence time, preferably not greater than 10, more preferably not greater than 6 minutes, still more preferably not greater than 3 minutes, and most preferably not greater than 2 minutes. In a particular embodiment of the invention, the flow rate in the CEXC step corresponds to a residence time not greater than about 2 minutes; in the HCIC step it is not greater than 3 minutes. While the flow rate is not essential to achieving purity levels obtainable by a method of the invention, rates are provided for purposes of guidance. One having ordinary skill in the art can modify the flow rate as needed.

The preferred measure of protein purification by a process of the present invention is the measure of host cell protein removal. The purified protein is preferably a homogenous composition as it is defined supra. Protein concentration of a sample at any stage of purification can be determined by any suitable method. Such methods are well known in the art and include: 1) colorimetric methods such as the Lowry assay, the Bradford assay, the Smith assay, and the colloidal gold assay; 2) methods utilizing the UV absorption properties of proteins; and 3) visual estimation based on stained protein bands on gels relying on comparison with protein standards of known quantity on the same gel. See e.g. Stoschek (1990), Quantitation of Protein, in Guide to Protein Purification, Methods in Enzymol. 182: 50-68. Protein contamination of a homogenous composition containing the protein of interest can be determined by various means know in the art, e.g., by enzyme-linked immunosorbent assay (ELISA; see e.g. Reen (1994), Enzyme-Linked Immunosorbent Assay (ELISA), in Basic Protein and Peptide Protocols, Methods Mol. Biol. 32: 461-466, which is incorporated herein by reference in its entirety).

The amount of DNA that may be present in a homogenous composition containing the protein of interest can be determined by any suitable method. For example, one can use an assay utilizing polymerase chain reaction. DNA can be reduced to levels that are lower than 10 pg/mg.

The protein thus recovered can be formulated in a biopharmaceutically acceptable composition and is used for various diagnostic, therapeutic or other uses known for such molecules.

After collection of the eluate containing the protein of interest, any proteins that may remain bound to the column can be released by stripping the chromatography medium using a solution comprising the buffer or salt used for chromatography, but at a higher molarity or modified pH. The column may then be regenerated using a solution (e.g., a regeneration solution) that will have the effect of releasing most or all proteins from the chromatography medium and reducing or eliminating any microbial contamination that may occur in the chromatography medium. Subsequently, the column may be rinsed and stored in a solution that discourages microbial growth. Such a solution may comprise sodium hydroxide, but other reagents can also be used, such as ethanol, sodium azide, benzyl alcohol or high concentration of lyotropic salts.

The following Example is provided for purposes of demonstrating the invention, and is not intended to be limiting.

Example

The present Example describes the purification of antibodies using a purification method of the present invention. Fully human antibodies were prepared against an activated T cell associated antigen (CTLA-4) and a tumor associated antigen (CD30) using Medarex's HuMAb Mouse®. Transfectomas were prepared using CHO DG44 cells. Cell culture was performed using synthetic, serum-free, defined medium at neutral pH (7 to 8) and conductivity between 10 and 16 mS/cm. The DG44 CHO cells were gown to a density of about 3 to $10 \times 10^6$ cells/ml. Cell culture was clarified by filtration using a 60MO2 CUNO filter (Meriden, Conn.). The resulting cell culture supernatant was concentrated and diafiltered in either 35 or 70 mM Sodium Phosphate, pH 6.2. For experiments where MEP Hypercel was used as the capture resin, the load was adjusted to pH 7 by titrating the concentrated and diafiltered cell culture supernatant with 1M NaOH. Purification of mixtures containing either of the two antibodies was performed in either direction as described below.

Tables 1 and 2 show examples of the two steps in a purification process of the invention for production of therapeutic grade protein material. In this process (A), the first non-affinity CEXC chromatography step was cationic exchange chromatography (Table 1) using Poros 50HS resin for capture, followed by a low pH hold using 1N HCl or glacial acetic acid to decrease the pH of the eluate to 3.4 to 3.6 and 2M Tris pH 9.0 to increase the pH of the fraction to 7.0. The second non-affinity step was HCIC (Table 2) using MEP HyperCel resin for capture. The low pH hold typically resulted in an increase of about 2 mS/cm in conductivity. The process was carried out using equilibration, loading, wash and elution buffers for the respective resin as indicated in Tables 1 and 2. Neither purification step used an in-process buffer exchange step, i.e., the sample proceeded from one chromatography step to the next with only pH manipulations as part of the low pH hold.

An alternate process (B) for production of therapeutic grade protein material was performed where the CEXC and HCIC chromatography steps were reversed, i.e., the steps in Table 2 were performed first followed by the steps in Table 1. The first non-affinity chromatography step was HCIC using MEP HyperCel resin for capture, as described in Table 2. A low pH hold using 1N HCl or glacial acetic acid was performed to decrease the pH of the MEP eluate to 3.4 to 3.6 followed by 2M Tris, pH 9.0 to increase the pH of the fraction to 6.2. The low pH hold typically resulted in an increase of about 2 mS/cm in conductivity. The second (CEXC) chromatography step was CEXC using Poros 50HS resin for polishing, as described in Table 1. The process was carried out using equilibration, loading, wash and elution buffers for the respective resin as indicated in the Tables. None of the purification steps in the alternate process included an in-process buffer exchange step, i.e., the sample proceeded from one chromatography step to the next with only pH manipulations as part of the low pH hold.

TABLE 1

Cation exchange chromatography for antibody capture or polishing: summary of major operational details. Binding capacity was constant at 15 mg/ml resin. Flow rates are expressed in corresponding residence times to provide wider experimental flexibility. Working temperature varied between 15-25° C. NaP = sodium phosphate.

| Step | Solution | pH | Cond. (mS/cm) | Vol. (CVs) | Maximum Residence Time (minutes) | Forward Processing Criteria |
|---|---|---|---|---|---|---|
| Sanitation | 1 N NaOH | ≧12 | N/A | ≧3 | 2 | Usually there is a hold of one hour, starting from the time the solution is applied onto the column. This step intends to clean the resin from bound contaminants, including those of biological origin. |
| Charge | 1 M NaCl | N/A | ~90 | ≧3 | 2 | NaCl removes NaOH from the column, while neutralizing and maintaining the ligand of the resin in connection with sodium ions. |
| Equilibration | 35 or 70 mM NaP | 6.2 | ~3 for the 35 mM NaP ~5.8 for the 70 mM NaP | ≧3 | 2 | Column is equilibrated when pH and conductivity are ±0.1 and ±0.2 mS/cm of the equilibrating buffer, respectively. Conductivity and pH ranges are important to bind the antibody, while minimizing the binding of host cell proteins. The highest concentration without compromising binding capacity should be used. |
| Load | Product | 6.2 | ~1 for MEP eluate ~3 for the 35 mM NaP load for anti-CD30 Ab ~5.8 for the 70 mM NaP load for anti-CTLA4 Ab | | 2 | Load is cell culture supernatant, concentrated and buffer exchanged in 35 or 70 mM Sodium Phosphate, pH 6.2, in accordance with the equilibration buffer, as CAPTURE. Before sterile filtration, the product can be filtered through a CUNO membrane. As a POLISH, load is MEP HyperCel eluate that underwent the low pH hold. |
| Post Load Wash 1 | 35 mM NaP with 0.1% Tween 80 | 6.2 | ~3 for the 35 mM NaP | ≧3 | 2 | Slower flow rate of the buffer containing Polysorbate 80 helps to reduce the DNA content of the final purified product. |
| Post Load Wash 2 | 35 mM NaP | 6.2 | 3-5.8 | ≧7 | 2 | Column is equilibrated when pH and conductivity are ±0.1 ±0.2 mS/cm of the equilibrating buffer. Conductivity and pH ranges are important to bind the antibody, while minimizing the binding of host cell proteins. |
| Elution | 35 mM MaP 40-75 mM NaCl | 6.2 | ~7 for 35 mM NaP, 40 mM NaCl for anti-CD30 Ab ~10.5 for 35 mM NaP, 75 mM NaCl for anti-CTLA4 Ab | ~5 | 2 | Collect the elution peak from rising $Abs_{280}$ to falling $Abs_{280}$ 20% above baseline. Do NOT collect the tailing of the peak to ensure lower CHOP level in elution. |
| Strip | 1 M NaCl | N/A | 69.1-95.9 | ≧5 | 2 | Removes tightly bound contaminants. |
| CIP | 1 N NaOH | ≧12 | N/A | ≧3 | 2 | Similar step to sanitization. |
| Storage | 0.1 N NaOH | ≧12 | N/A | ≧3 | 2 | Alkalinity of this solution does not allow microbial growth but maintains resin integrity. |

TABLE 2

MEP HyperCel chromatography for antibody capture or polishing: summary of major details. Binding capacity was constant at 15 mg/ml resin. Flow rates are expressed in corresponding residence times to provide wider experimental flexibility. Working temperature varied between 15-25° C. NaP = sodium phosphate.

| Step | Solution | pH | Cond. (mS/cm) | Vol. (CVs) | Maximum Residence Time (minutes) | Forward Processing Criteria |
|---|---|---|---|---|---|---|
| Sanitization | 1 N NaOH | ≧12 | N/A | ≧3 | 3 | Usually there is a hold of one hour, starting from the time the solution is applied onto the column. This step intends to clean the resin from bound contaminants, including those of biological origin. |
| Charge | 1 M NaCl | N/A | ~90 | ≧3 | 2 | NaCl removes NaOH from the column, while neutralizing and maintaining the ligand of the resin in connection with sodium ions. |
| Equilibration | 35 or 70 mM NaP | 7.0 | ~4 (35 mM NaP) ~8 (70 mM NaP) | ≧3 | 3 | Column is equilibrated when pH and conductivity are ±0.1 and ±0.2 mS/cm of the equilibrating buffer, respectively. |
| Load | Product | 7.0 | ~4 for the 35 mM NaP used in capture for | | 3 | Load is cell culture supernatant, concentrated and buffer exchanged in 35 or 70 mM Sodium Phosphate, pH 6.2, and adjusted to pH 7.0, as |

TABLE 2-continued

MEP HyperCel chromatography for antibody capture or polishing: summary of major details. Binding capacity was constant at 15 mg/ml resin. Flow rates are expressed in corresponding residence times to provide wider experimental flexibility. Working temperature varied between 15-25° C. NaP = sodium phosphate.

| Step | Solution | pH | Cond. (mS/cm) | Vol. (CVs) | Maximum Residence Time (minutes) | Forward Processing Criteria |
|---|---|---|---|---|---|---|
| | | | anit-CD30 Ab ~8 for the 70 mM NaP used in capture for anti-CTLA4 Ab ~10 for the CEX eluate used in polishing | | | CAPTURE. Before sterile filtration, the product can be filtered through a CUNO membrane. As a POLISH, load is CEXC eluate that underwent a low pH hold. |
| Post Load Wash 1 | 70 mM NaP | 7.0 | ~8 | ≧5 | 3 | Optional. |
| Post Load Wash 2 | 35 mM NaP | 7.0 | ~4 | ≧5 | 3 | pH and conductivity of these buffers are very crucial for contaminants (CHOP) removal. |
| Post Load Wash 3 | 5 mM NaP | 7.0 | <1 | ≧5 | 3 | Lower conductivity of the buffer removes more hydrophilic contaminants and reduces the conductivity of the system, prior to elution. |
| Elution | 10 mM Na Acetate | 5.2 | <1 | ~3 to 5 | 3 to 6 | Collect the elution peak from rising $A_{280}$ to falling $A_{280}$ 20% above baseline. Do NOT collect the tailing of the peak to ensure lower CHOP level in elution. Slow flow rate minimizes the host cell protein in the elution. |
| Strip | 100 mM NaCitrate | 3.0 | ~4 | ≧5 | 3 | Removes tightly bound contaminants. |
| CIP | 1 N NaOH | ≧12 | N/A | ≧3 | 3 | Similar step to sanitization. |
| Storage | 0.1 N NaOH | ≧12 | N/A | ≧3 | 3 | Alkalinity of this solution does not allow microbial growth but maintains resin integrity. |

Using a standard ELISA assay to confirm CHOP levels, PCR to confirm DNA levels, and HPLC-SEC to confirm the monomer purity of the antibody, each of the two purification procedures A and B, achieved a homogenous composition, containing less than 100 ppm host cell protein (see Table 3 below), less than 10 pg DNA/mg antibody and greater than 99% monomer, which permits further processing and formulation of the purified material to a therapeutic grade product. The contaminant concentration after the first step varied between 200 and 1500 ng/mg for CHOPs and 95 to 100% monomer. The results for processes A and B using two different fully human monoclonal antibodies are reported in Table 3.

TABLE 3

Summary of contaminant removal using suggested purification schemes.

| Process | Parameter | (anti-CTLA-4 Ab) | (anti-CD30 Ab) |
|---|---|---|---|
| CEXC→HCIC | % Overall Recovery | 74 | 68 |
| | Final CHOP (ng/mg) | 30.8 | 44.2 |
| | Final DNA (pg/mg) | <10.00 | <10.00 |
| | Final Purity (% Monomer by HPLC-SEC) | 100.00 | 99.55 |
| HCIC→CEXC | Overall Recovery | 84.8 | 74.5 |
| | Final CHOP (ng/mg) | 69.9 | 42.6 |
| | Final DNA (pg/mg) | <10.00 | <10.00 |
| | Final Purity (% Monomer by HPLC-SEC) | 100.00 | 99.82 |

What is claimed is:

1. A method for purifying a target protein from a mixture, which comprises the target protein and one or more contaminants, wherein the contaminants comprise host cell proteins, said method comprising purification steps consisting of:

(a) subjecting the mixture to a cation exchange chromatography step and a hydrophobic charge induction chromatography step, in either order, wherein the hydrophobic charge induction chromatography step or the cation exchange chromatography step uses an elution buffer that elutes the host cell proteins differentially in relation to the target protein, and wherein the tailing of the $Abs_{280}$ peak of the target protein is not collected at less than 20% above the baseline as measured by $Abs_{280}$ relative to the maximum of the peak height; and (b) isolating the target protein to a purity of about 100 parts per million (ppm) or less of host cell proteins.

2. The method of claim 1, wherein the mixture is subjected to the hydrophobic charge induction chromatography step first.

3. The method of claim 1, wherein the mixture is subjected to the cation exchange chromatography step first.

4. The method of claim 1, wherein the target protein is isolated to a purity of about 10 pg/mg or less of nucleic acids.

5. The method of claim 1, which further includes a viral inactivation step.

6. The method of claim 5, wherein the viral inactivation step is an in-process step.

7. The method of claim 1, wherein the mixture is prepared from a cell culture supernatant.

8. The method of claim 1, wherein the cation exchange chromatography step is performed at a pH range from 3 to 10.

9. The method of claim 1 wherein the cation exchange chromatography step is performed at a pH range from 4.0 to 8.0.

10. The method of claim 1, wherein the hydrophobic charge induction chromatography is performed at a pH range from 3 to 10.

11. The method of claim 1, wherein the hydrophobic charge induction chromatography is performed using at a pH range from 4.0 to 9.0.

12. The method of claim 1, wherein the cation exchange chromatography step includes a cation exchange chromatography column and the target protein binds to the column at pH 3 to 9 and at a conductivity range from 0.1 to 40 mS/cm.

13. The method of claim 1, wherein the cation exchange chromatography step includes a cation exchange chromatography column and the target protein binds to the column at pH 4.0 to 8.0 and at a conductivity from 0.5 to 10 mS/cm.

14. The method of claim 1, wherein the hydrophobic charge induction chromatography step includes a hydrophobic charge induction chromatography column and the target protein binds to the column at pH 5 to 10 and at a conductivity range from 0 to 90 mS/cm.

15. The method of claim 1, wherein the hydrophobic charge induction chromatography step includes a hydrophobic charge induction chromatography column and the target protein binds to the column at pH 6 to 9 and conductivity range from 2 to 9 mS/cm.

16. The method of claim 1, wherein the cation exchange chromatography step includes a cation exchange chromatography column and the target protein is bound to the column and the column is washed using a wash buffer having a pH range from 3 to 9 and a conductivity range from 0.1 to 40 mS/cm.

17. The method of claim 1, wherein the cation exchange chromatography step includes a cation exchange chromatography column and the target protein is bound to the column and the column is washed using a wash buffer having a pH range from 4.0 to 8.0 and a conductivity range from 0.5 to 10 mS/cm.

18. The method of claim 1, wherein the hydrophobic charge induction chromatography step includes a hydrophobic charge induction chromatography column and the target protein is bound to the column and the column is washed using a wash buffer having a pH range from 5 to 10 and a conductivity range from 0 to 90 mS/cm.

19. The method of claim 1, wherein the hydrophobic charge induction chromatography step includes a hydrophobic charge induction chromatography column and the target protein is bound to the column and the column is washed using a wash buffer having a pH range from 6 to 9 and a conductivity range from 0.1 to 9 mS/cm.

20. The method of claim 1, wherein the cation exchange chromatography step includes a cation exchange chromatography column and the target protein elutes from the column at a pH range from 3 to 10 and a conductivity range from 0.1 to 40 mS/cm.

21. The method of claim 1, wherein the cation exchange chromatography step includes a cation exchange chromatography column and the target protein elutes from the column at a pH range from 4.0 to 8.0 and a conductivity range from 5 to 15 mS/cm.

22. The method of claim 1, wherein the hydrophobic charge induction chromatography step includes a hydrophobic charge induction chromatography column and the target protein elutes from the column at a pH range from 3.0 to 7.0 and a conductivity range from 0 to 20 mS/cm.

23. The method of claim 1, wherein the hydrophobic charge induction chromatography step includes a hydrophobic charge induction chromatography column and the target protein elutes from the column at a pH range from 4.0 to 6.0 and a conductivity range from 0.1 to 2.0 mS/cm.

24. The method of claim 1, wherein the cation exchange chromatography step employs a cation exchange ligand selected from sulfonate, carboxylic, carboxymethyl sulfonic acid, sulfoisobutyl, sulfo ethyl, carboxyl, sulphopropyl, sulphonyl, sulphoxyethyl and orthophosphate.

25. The method of claim 1, wherein the cation exchange chromatography step is performed on a cation exchange resin selected from Poros HS, Poros S, carboxy-methyl-cellulose, BAKERBOND ABX™, sulphopropyl immobilized on agarose and sulphonyl immobilized on agarose, MonoS, MiniS, Source 15S, 30S, SP Sepharose, CM Sepharose, BAKERBOND Carboxy-Sulfon, WP CBX, WP Sulfonic, Hydrocell CM, Hydrocel SP, UNOsphere S, Macro-Prep High S, Macro-Prep CM, Ceramic HyperD S, Ceramic HyperD CM, Ceramic HyperD Z, Trisacryl M CM, Trisacryl LS CM, Trisacryl M SP, Trisacryl LS-38-SP, Spherodex LS SP, DOWEX Fine Mesh Strong Acid Cation Resin, DOWEX MAC-3, Matrex Cellufine C500, Matrex Cellufine C200, Fractogel EMD S03-, Fractogel EMID SE, Fractogel EMD COO-, Amberlite Weak and Strong Cation Exchangers, Diaion Weak and Strong Cation Exchangers, TSK Gel SP-5PW-HR, TSK Gel SP-5PW, Toyopearl CM (650S, 650M, 650C), Toyopearl SP (650S, 650M, 650C), CM (23, 32, 52), SE (52, 53), P11, Express-Ion C and Express-Ion S.

26. The method of claim 1, wherein the hydrophobic charge induction chromatography step employs a hydrophobic charge induction chromatography ligand comprising an ionizable aromatic or heterocyclic structure which has an aliphatic chain and at least one sulfur atom.

27. The method of claim 1, wherein the hydrophobic charge induction chromatography step is performed using a hydrophobic charge induction resin MEP HyperCel.

28. The method of claim 1, wherein the contaminants are selected from host cell metabolites, host cell constitutive proteins, nucleic acids, endotoxins, product related contaminants, lipids, and media additives or media derivatives.

29. The method of claim 1, wherein the target protein is an antibody or antibody fragment.

30. The method of claim 29 wherein the antibody is a monoclonal antibody.

31. The method of claim 29 wherein the antibody is a fully human antibody.

32. The method of claim 29 wherein the antibody is an anti-CTLA4 antibody.

33. The method of claim 29 wherein the antibody is selected from the group consisting of single-chain antibody molecules, diabodies, linear antibodies, bispecific antibodies and multispecific antibodies.

34. The method of claim 29 wherein the antibody fragment is selected from the group consisting of a Fab, Fab', F(ab')2 and Fv.

35. The method of claim 29 wherein the antibody is an anti-CD30 antibody.

36. The method of claim 1, wherein the target protein is an immunoadhesin.

37. The method of claim 1, further comprising the step of formulating the isolated protein into a pharmaceutical composition.

38. The method of claim 1, wherein in step (a), the tailing of the $Abs_{280}$ peak of the target protein is not collected at less than 25% above the baseline of $Abs_{280}$ relative to the maximum of the peak height.

* * * * *

UNITED STATES PATENT AND TRADEMARK OFFICE
CERTIFICATE OF CORRECTION

| | | |
|---|---|---|
| PATENT NO. | : 8,129,508 B2 | Page 1 of 1 |
| APPLICATION NO. | : 11/918155 | |
| DATED | : March 6, 2012 | |
| INVENTOR(S) | : Alahari Arunakumari et al. | |

It is certified that error appears in the above-identified patent and that said Letters Patent is hereby corrected as shown below:

In the Claims:

Claim 25:
    Column 28, line 13, delete "Hydrocel" and insert --Hydrocell--, therefor.

Claim 25:
    Column 28, line 19, delete "EMID" and insert --EMD--, therefor.

Signed and Sealed this
Fourteenth Day of August, 2012

David J. Kappos
*Director of the United States Patent and Trademark Office*